(12) United States Patent
Wilke

(10) Patent No.: US 8,926,810 B2
(45) Date of Patent: Jan. 6, 2015

(54) REFERENCE ELECTRODE

(75) Inventor: Stefan Wilke, Halle (DE)

(73) Assignee: Endress + Hauser Conducta Gesellschaft für Mess—und Regeltechnik mbH + Co. KG, Gerlingen (DE)

( * ) Notice: Subject to any disclaimer, the term of this patent is extended or adjusted under 35 U.S.C. 154(b) by 743 days.

(21) Appl. No.: 13/141,359

(22) PCT Filed: Nov. 27, 2009

(86) PCT No.: PCT/EP2009/065960
§ 371 (c)(1),
(2), (4) Date: Sep. 8, 2011

(87) PCT Pub. No.: WO2010/072509
PCT Pub. Date: Jul. 1, 2010

(65) Prior Publication Data
US 2011/0308947 A1 Dec. 22, 2011

(30) Foreign Application Priority Data
Dec. 22, 2008 (DE) .......................... 10 2008 055 082

(51) Int. Cl.
*G01N 27/403* (2006.01)
*G01N 27/401* (2006.01)
*G01N 27/30* (2006.01)

(52) U.S. Cl.
CPC .............. *G01N 27/401* (2013.01); *G01N 27/30* (2013.01); *G01N 27/403* (2013.01)
USPC .......................................... 204/406; 204/435

(58) Field of Classification Search
CPC ...... G01N 27/301; G01N 27/32; G01N 27/40
See application file for complete search history.

(56) References Cited

U.S. PATENT DOCUMENTS

| 4,002,547 A | * | 1/1977 | Neti et al. ..................... 204/435 |
| 4,177,126 A | | 12/1979 | Imaki |
| 4,592,824 A | | 6/1986 | Smith |
| 4,836,908 A | * | 6/1989 | Ford .............................. 204/435 |
| 2002/0179457 A1 | | 12/2002 | Heller |

(Continued)

FOREIGN PATENT DOCUMENTS

| CH | 6 80 311 A5 | 7/1992 | |
| DE | 3206100 A1 | * 9/1983 | ............. G01N 27/30 |

(Continued)

OTHER PUBLICATIONS

JPO computer-generated English language translation of Uchihara et al. JP 2008-008796 A, patent published Jan. 17, 2008.*

(Continued)

*Primary Examiner* — Alex Noguerola
(74) *Attorney, Agent, or Firm* — Bacon & Thomas, PLLC

(57) ABSTRACT

A reference electrode, especially for a potentiometric measuring cell, comprising: a housing, which surrounds a housing interior, which contains a reference electrolyte and at least a part of a sensing system for sensing a potential of the reference electrode. The reference electrolyte is in contact with a medium surrounding the housing, especially a measured medium, via at least one bore traversing through a housing wall of the housing, and wherein the bore has an inner diameter of no more than 50 μm at its narrowest point and a length of no more than 200 μm.

21 Claims, 6 Drawing Sheets

(56) References Cited

U.S. PATENT DOCUMENTS

2004/0011647 A1  1/2004  Broadley
2004/0011670 A1  1/2004  Broadley
2004/0195098 A1  10/2004 Broadley

FOREIGN PATENT DOCUMENTS

| DE | 198 01 344 | A1 |   | 7/1999 |   |   |
|----|------------|----|---|--------|---|---|
| DE | 100 53 979 | A1 |   | 5/2002 |   |   |
| DE | 102 07 624 | A1 |   | 9/2003 |   |   |
| EP | 0105434    | A2 | * | 4/1984 | ............. | G01N 27/30 |
| JP | 2008-008796| A  | * | 1/2008 | ........... | G01N 27/401 |

OTHER PUBLICATIONS

EPO computer-generated English language translation of Prof. Dr. Franz-Josef Haberich DE 3206100 A1, patent published Sep. 1, 1983.*
EPO computer-generated English language translation of Buehler et al. CH 680311 A5, patent published Sep. 1, 1983.*
German Search Report for application No. 20 2008 055 082.5 published Jan. 10, 2011.
International Search Report for International application No. PCT/EP2009/065960 published Feb. 19, 2010.
English translation of International Preliminary Report for International application No. PCT/EP2009/065960 published Jul. 11, 2011.

* cited by examiner

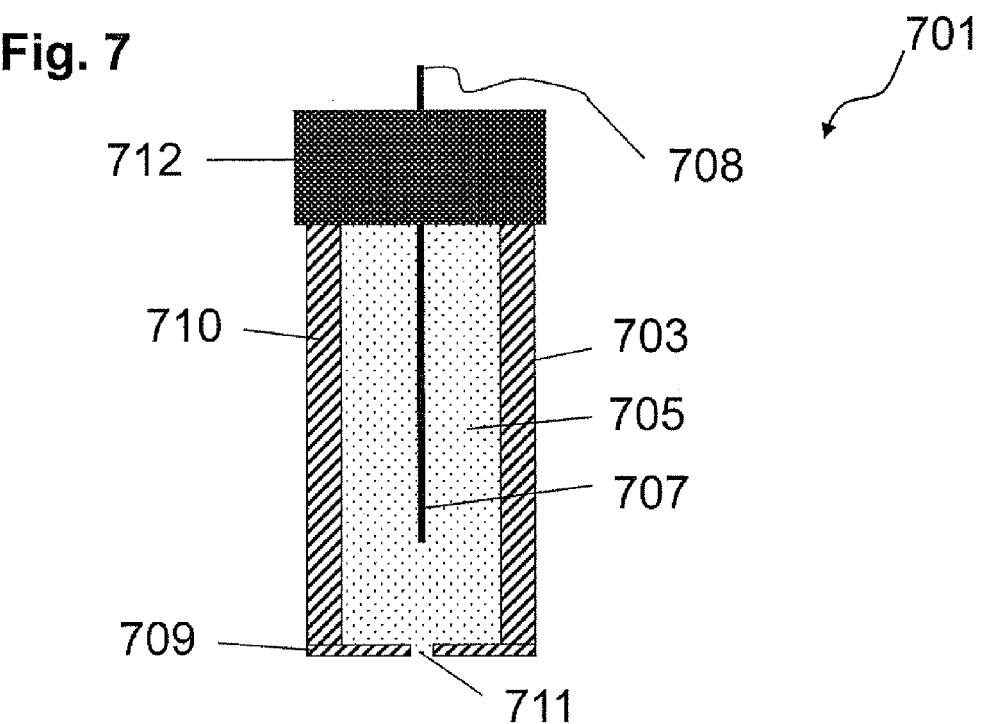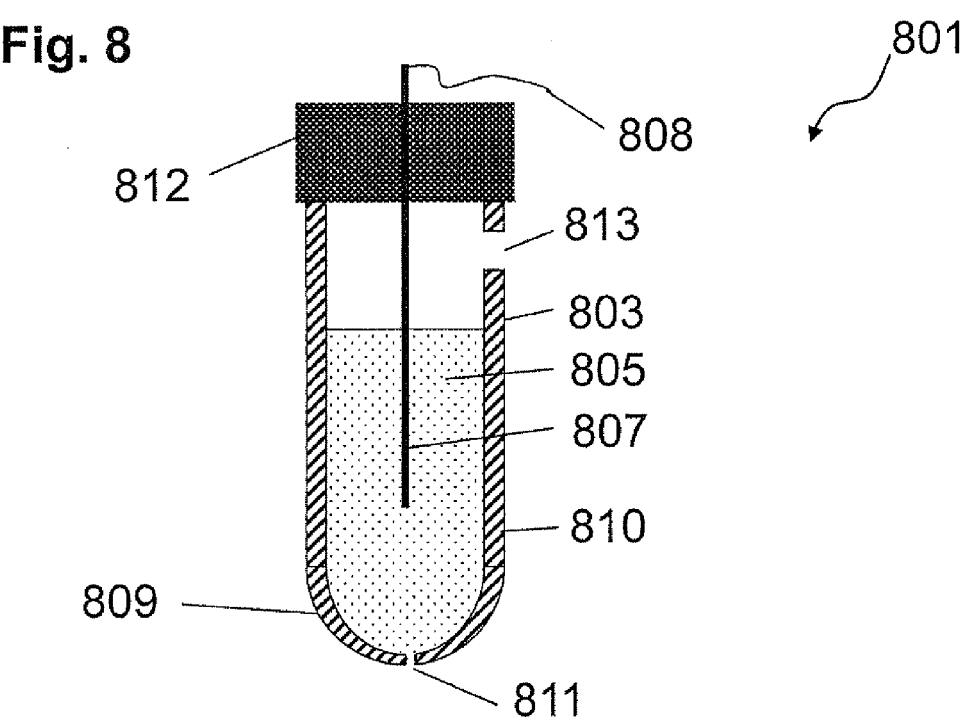

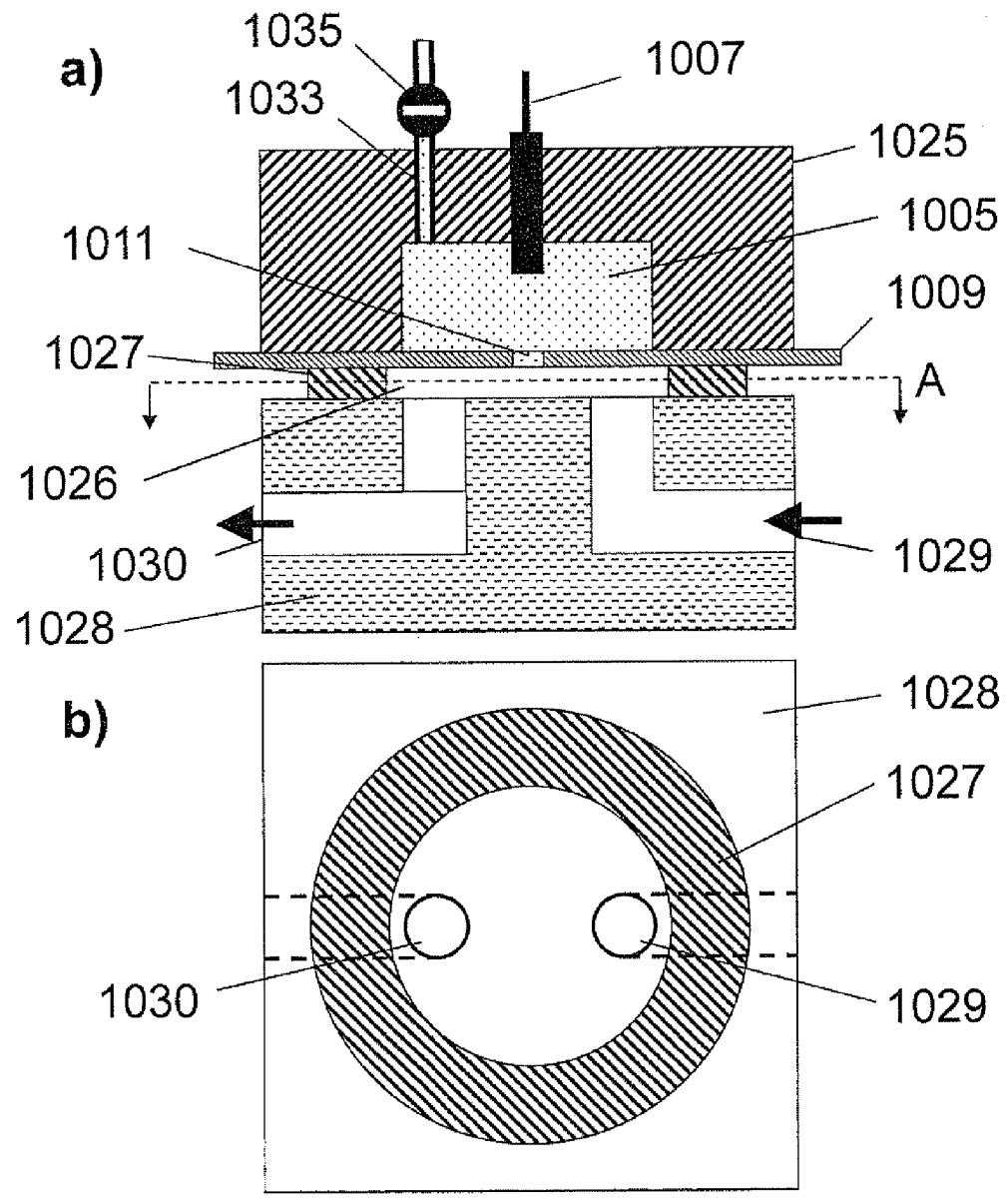

REFERENCE ELECTRODE

TECHNICAL FIELD

The present invention relates to a reference electrode, especially for a potentiometric measuring cell, and includes a housing surrounding a housing interior containing a reference electrolyte and at least a part of a potential sensing system for sensing a potential of the reference electrode.

BACKGROUND DISCUSSION

Reference electrodes serve to deliver a constant reference potential for measurements in potentiometric measuring cells having one or a plurality of measuring electrodes. They are frequently used in many applications as rod shaped reference electrodes or, combined with a measuring electrode to form what is called a single rod, measuring chain. Measuring electrodes, together with which the reference electrodes are applied, include, for example, pH electrodes or ion selective electrodes for determining cations such as sodium, potassium, calcium or anions such as chloride, fluoride, nitrate and carbonate. For example, such electrode combinations serve to determine corresponding ion concentrations in aqueous solutions or media containing water, as well as in natural water, swimming pools, waste water, or product streams.

It is known that the part of the reference electrode, which is brought into contact with a sample (also referred to as the measured medium in the following) when performing the measuring, must assure an electrolytic contact of the reference electrolyte in the reference electrode with the sample. This contact location, where the liquid contact between the reference electrolyte of the reference electrode and the measured medium occurs, is referred to as the diaphragm. Frequently the diaphragm is embodied as a plug made from a networked hydrogel, as a porous ceramic or plastic dowel, as a gap or as ground glass.

As is known, the ion concentration in the measured medium is determined with a measuring cell constructed of a measuring electrode, namely an ion selective electrode or a pH electrode, and a reference electrode, based on a change of the potential difference between the measuring electrode and the reference electrode. The potential of the measuring electrode is dependent on the concentration of the ion type to be determined in the measured medium and, in an ideal case, is not influenced by the presence of disturbing ions, while the potential of the reference electrode is not influenced by the concentration of the type of ion to be determined or the disturbing ions. Accordingly, the potential difference between the measuring electrode and the reference electrode changes in this ideal case exclusively due to the change of the potential of the measuring electrode as a result of changed concentrations of the ions to be determined, while the potential of the reference electrode must remain unchanged, so that the concentration of the ion to be determined in the sample solution can be directly read off based on the potential difference following a corresponding calibrating.

Accordingly, a change of the potential of the reference electrode leads to a corruption of the measurement results. The operative region for such a change of the potential of the reference electrode is the region of the diaphragm, in which the reference electrolyte contained in the reference electrode is in direct or indirect liquid contact with the measured medium.

Loss of reference electrolyte from the reference electrode in the region of the diaphragm leads to a decrease in the concentration of the reference electrolyte, as long as it is not cancelled by an external electrolyte supply or a supply of undissolved salt in the reference electrolyte. For example, since the voltage of a silver/silver chloride reference electrode (also known as a Ag/AgCl reference electrode) filled with potassium chloride solution (i.e. a reference electrode, which most often contains a 3 molar potassium chloride solution as a reference electrolyte and has a sensor system in fixed contact with silver chloride, e.g. a silver chloride coated silver electrode) depends approximately on the logarithm of the concentration of the potassium chloride; a decrease in the concentration of the potassium chloride is associated with an increase of the electrode potential of the reference electrode, which in turn is noticeable as drift of the measuring chain voltage or the measured value. In measurements of the concentration of univalent ions by means of ion selective electrodes, a voltage measurement error of only 1 mV already corresponds to a relative concentration measurement error of 4%. In the case of online measurement technology, which is used, as a rule, in process measurement technology, the reference electrode is continually immersed in the measured medium. In this case, the decline in the concentration of the reference electrolyte can limit the lifetime or the service life of the reference electrode in the measured medium or require frequent recalibration or readjustment of the measuring chain in which the reference electrode is a component.

Due to the solubility of silver chloride in the relatively highly concentrated potassium chloride solution, the reference electrolyte of a silver/silver chloride reference electrode has, in general, 0.3 to 1 g/l dissolved silver chloride. If this reference electrolyte comes in contact with a measured medium which contains proteins, sulfides, iodides or other components, which react with silver to form a difficulty soluble compound, then these difficulty soluble silver compounds precipitate and clog the pores of the diaphragm. Also, in given cases, suspended materials present in the measured medium or other macroscopic fouling of the measured medium can contaminate the diaphragm.

Also, strongly oxidizing or reducing materials, which reach the housing interior of the reference electrode through the electrolytic connection between the reference electrolyte and the measured solution, can degrade the function of the reference electrode, since they bring about a redox potential in the sensor Furthermore, a diffusion potential forms at the diaphragm between the reference electrolyte and the measured medium. The size and magnitude thereof depend, among other things, on the type and concentrations of the ions in the reference electrolyte and in the measured medium, on the type and geometric shape of the diaphragm and on the flow conditions. An attempt to minimize the diffusion potential or to hold it constant is made through the choice of a suitable reference electrolyte and a suitable embodiment of the diaphragm. Relatively low diffusion potentials can be achieved when a concentrated salt solution is used as a reference electrolyte, and moreover, when the cation and anion of the salt dissolved in the reference electrolyte have almost equal ionic mobilities. For this reason, a 3 to 4 molar aqueous solution of potassium chloride is frequently used as reference electrolyte or as bridge electrolyte in salt bridges. In potentiometric measuring, in general, the greatest part of the total measurement uncertainty rests on the uncertainty of the diffusion potential, even in the case of a carefully selected reference electrolyte.

The clogging by slightly soluble materials or other impurities previously described can significantly influence the diffusion potential in diaphragms made from porous materials, and therewith enlarge the measurement uncertainty or even corrupt the measured values to an unacceptable degree.

Numerous known approaches aim for reaching a high stability of the electrode voltage over time, i.e. a low sensor drift, and a long service life, by means of a special shaping of the diaphragm, in the case of which both the exit of the reference electrolyte into the measured medium and the entry of sample components in the reverse direction is small.

One the oldest known approaches, e.g. in K. Schwabe: pH-Messtechnik, Theodor Steinkopff, Dresden, 1976, is to connect the reference electrolyte and the measured solution via a plug shaped diaphragm made of a networked hydrogel. The gel plug suppresses convective mixing of the two solutions and at the same time represents a certain degree of diffusion barrier. In spite of this, the extraction of the electrolyte and the entry of disturbing components from the measured medium electrodes are still relatively high in the case of such reference.

Another possibility of an electrolytic connection between the housing interior of the reference electrode and the measured medium is in the embodying of the diaphragm as a gap, most often as an annular gap, or as a ground glass connection. Gap and ground diaphragms have a number of advantages, among these being that they are suitable for measurements in ion deficient media, the flow velocity of the measured solution scarcely influences the voltage; and the diffusion potentials and the electrical resistance are small. Additionally, ground diaphragms having a releasable ground piece are easily cleaned.

In the case of reference electrodes having a liquid reference electrolyte and a ground diaphragm, however, a sizeable loss of the electrolyte solution from the housing interior happens, so that the electrolyte must be replenished at times. Ground diaphragms are therefore suitable mainly for laboratory applications, however, less so for process measurements technology, in which maintenance free service life of the reference electrode is required for as long as possible.

If a gel electrolyte is provided in a reference electrode having a gap diaphragm, the loss of electrolyte from the housing interior is largely suppressed. There remains, however, a relatively strong diffusion of KCl from the reference electrolyte, from the housing interior into the measured medium, which leads to a potential drift of the reference electrode due to the concentration decline of the KCl. Moreover, components of the measured medium can diffuse into the electrolyte in the housing interior via the gap diaphragm.

A further approach for reducing mixing of reference electrolyte and measured medium is to make the diffusion path between the measured medium and the interior of the reference electrode as long as possible. Such a reference electrode is described in DE 102 07 624 A1, for example. In the case of spatially extended diffusion zones, however, an essentially constant diffusion potential, and, therewith, a stable, voltage measured value of the measuring chain, arises only gradually. Thus, in many cases the time response behavior of the potentiometric pH value measurement is determined not by the tuning processes of the pH selective, glass membrane of the measuring electrode, but, instead, by the tuning processes at the diaphragm of the reference electrode between reference electrolyte and measured medium.

A reference electrode having a single pore as a diaphragm, through which reference electrolyte escapes with a well defined and constant velocity, is described in CH 680 311 A5. In such case, length and diameter of the pore are so matched to one another that the electrical resistance of the electrolyte within the pore does not exceed a maximum range. For a pore diameter of 0.05 to 0.5 mm, the preferred length of the pore is between 0.5 and 12 mm, especially preferably between 7 and 8 mm.

Additionally, through the flowing out of the reference electrolyte with a constant velocity of 1 to 15 m per day, a constant diffusion potential and an equally constant response time should be assured. Through the significantly smaller internal surface area of the single pore compared to a porous material, sensitivity against fouling of the reference electrode by particles or disturbing substances from the measured medium should be reduced.

However, this embodiment has disadvantages: Through the flowing out of the reference electrolyte into the measured medium, the measured medium can be relatively strongly contaminated with the reference electrolyte. Furthermore, a pressure difference between the reference electrolyte in the interior of the reference electrode and the measured medium is required to assure flow of the reference electrolyte from the housing interior of the reference electrode into the measured medium. In the case of electrodes for use in the laboratory, such a pressure difference can be produced, in that the housing of the reference electrode has an opening in a region which is not immersed in the measured medium, through which a pressure equalization between the atmosphere and the housing interior of the reference electrode is achieved. The hydrostatic pressure of the reference electrolyte affected by a height difference of a few centimeters between the reference electrolyte in the housing interior of the reference electrode and the measured medium suffices for the reference electrolyte to flow out from the housing interior through the pore. In the case of applications in process measurements technology, in contrast, frequently an internal pressure production, for example, by means of a gas evolution cell in the housing interior; or an external pressure loading by means of pressurized gas; or electrolytes under pressure from an outer supply vessel, is required. However, these are relatively complex solutions, and therefore susceptible to defects and expensive. In addition to the apparatus effort, which must be pursued, in order to assure a continual flow of the reference electrolyte from the housing interior of the reference electrode, further effort is necessary, in order to limit the flow velocity to a maximum of 15 ml per day.

SUMMARY OF THE INVENTION

Consequently, an object of the invention is to provide a reference electrode, which overcomes the disadvantages of the state of the art. Especially, a reference electrode should be specified, which assures a simple construction and therewith a simple and cost effective manufacturing, a high accuracy of measurement and a low drift over an acceptable period of time in process measurement technology, and which, thus, is suitable for use in the process measurement technology.

The object is achieved by a reference electrode, especially a reference electrode for a potentiometric measuring chain, comprising:

a housing surrounding a housing interior containing a reference electrolyte and at least a part of a sensing system for sensing a potential of the reference electrode;

wherein the reference electrolyte is in contact with a medium surrounding the housing, especially a measured medium, via at least one traversing bore passing through a housing wall of the housing;

and wherein the bore has an inner diameter of no more than 50 µm at its narrowest point and a length of no more than 200 µm, especially less than 100 µm.

In measurement operation, the housing of the reference electrode is immersed at least so far into a measured medium that the measured medium is in contact with the reference electrolyte via the traversing bore. In other words, the housing of the reference electrode has an immersion region, which is brought in contact with the measured medium when performing a measurement, and to which belongs at least one region surrounding the traversing bore of the housing wall.

The housing of the reference electrode can comprise an electrically insulating material, such as e.g. glass or a synthetic material, such as e.g. plastic. Here and in the following, a bore is understood to mean, besides an opening manufactured by means of a rotating tool, also a traversing opening produced by any other known method in the state of the art, such as e.g. laser ablation, etching or electrical discharge machining, which produces a connection between the housing interior and the medium surrounding the housing. Furthermore, in the sense of this application, an opening already present in the housing wall due to material properties, such as e.g. a pore, is also understood to be a bore.

A traversing bore passing through the housing wall includes an exit into the housing interior, also referred to as an internal exit in the following, and an exit to the environment of the housing, also referred to as an external exit in the following.

The distance between the internal and the external exits of the bore is to be understood as the length of the bore. The bore has a length of 1 to 200 µm, especially of 1 to 100 µm, especially of 1 to 50 µm.

The inner diameter of the bore corresponds to the diameter of its cross sectional area.

A high hydrodynamic resistance and a high diffusion resistance are achieved, in spite of the short length of no longer than 200 µm, especially no longer than 100 µm, through the small bore diameter of 50 µm or less. In this way, the loss of reference electrolyte into the medium, or the entry of disturbing substances from the surrounding medium into the reference electrolyte, is strongly reduced.

It was determined in measurements that in the case of a reference electrode with an single bore of about 3.5 µm in diameter and 12 µm in length, the loss of potassium chloride from an aqueous, 3 molar potassium chloride solution as the reference electrolyte only amounted to about 0.2 µmol per day. If the reference electrode was filled with a gel reference electrolyte, the loss of potassium chloride amounted to only about 0.3 nmol per day. In the case of a reference electrode with a conventional porous PTFE diaphragm after a soak time of 3 months a loss of 6 µmol/day was measured, thus about 20,000 or 30,000 times as much.

The concentration of the reference electrolyte in the housing interior of the reference electrode of the invention, thus, diminishes only very slowly in comparison to conventional, porous diaphragms. Because of the dependence of the reference electrode potential on the concentration of the potassium chloride of the reference electrolyte mentioned above, the very slow change of the potassium chloride concentration, thus, leads to a reduced drift of the measuring chain voltage, and, respectively, of the measured value compared to reference electrodes with porous diaphragms known from the state of the art.

Moreover, due to the reduced electrolyte outflow in comparison to the reference electrodes known from the state of the art with a porous diaphragm, respectively, a gap or ground diaphragm, the service life of the reference electrode is lengthened.

Additionally, the penetration of damaging substances from the surrounding medium into the internal housing of the reference electrode is also reduced due to the small material transport through the bore. Because of the essentially smaller inner surface of the bore in comparison to porous diaphragms, especially in the case of a small length of the bore of less than 200 µm, especially less than 100 µm, the susceptibility of the bore to fouling is, similarly to the case of the single pore described in CH 680 311 A5, further reduced compared to conventional diaphragms.

A further advantage of the described reference electrode is that it has only a small diffusion potential at the diaphragm between the reference electrolyte and the surrounding medium. The diffusion potential is largely independent of the flow velocity and the composition of the surrounding medium, especially the measured medium, and adjusts quickly. This is true also for measured media with low electrolyte concentration, which correspondingly have a low conductivity.

Thus, the described reference electrode has comparable advantages to the reference electrode known from CH 680 311 A5 as regards fouling tendency of the diaphragm, stability of the diffusion potential and independence of the electrode potential from the flow of the measured medium. The permanent outflow of the reference electrolyte with a predetermined constant outflow velocity can, thus, be omitted in the case of comparable behavior of the reference electrode. This brings the large advantage that loss of reference electrolyte is clearly reduced compared to the reference electrode described in CH 680 311 A5. Furthermore, means for adjusting the outflow velocity, such as pressure cartridges or flow limiters, can be omitted, so that the construction of the reference electrode for purposes of use in process measurements technology can be significantly simplified.

A further advantage of the reference electrode of the invention having at least one bore with a length of no more than 200 µm lies in the simpler manufacturability of such bores compared to longer bores having a length of several mm. The bore can be embodied in a film, for example, wherein the film can then be connected as a housing wall with another housing part to form the electrode housing of the reference electrode. The film can have a thickness between 5 and 50 µm, preferably between 5 and 20 µm.

In an embodiment, the length and the diameter of the bore are matched to one another in such a manner that in the case of diffusion of a substance through the bore, spherical sector shaped, especially hemispherical, diffusion profiles form bordering on the bore both medium-side as well as also interior-side. A spherical sector means one formed from a spherical segment (spherical cap) and a cone with the circle of the spherical segment as its base and the sphere center as its apex. A limiting case is the hemisphere, which is here understood as a special case of a spherical sector. Because of the spherical sector shaped or hemispherical character of the diffusion in the two spherical sector shaped or hemispherical volume elements, which, in each case, adjoin the external and the internal exits of the bore, the material transport occurs there very intensively, so that within a short time a steady state concentration profile and therewith also stable diffusion potentials form.

In an additional embodiment, the bore has a cylindrical or conical shape with a circularly shaped, or an almost circularly shaped, cross section.

In an additional embodiment, the reference electrolyte comprises an aqueous solution of a salt, especially a 3 to 4 molar potassium chloride solution, or a gel reference electrolyte. The material transport through the diaphragm caused by convection can be significantly reduced when, for example, a gel reference electrolyte is used, which contains a viscosity increasing or solidifying hydrogel, so that it is dimensionally stable.

In an additional embodiment, the reference electrolyte is in contact with the medium surrounding the housing via one or a number of traversing bores passing through a housing wall of the housing, wherein the sum of the cross sectional areas of all traversing bores at their narrowest point(s) is, in each case, between 0.5 to 2000 $\mu m^2$, especially 0.5 to 200 $\mu m^2$, especially 0.5 to 20 $\mu m^2$. If an aqueous salt solution is provided as a reference electrolyte, then the sum of the cross sectional areas is preferably between 0.5 and 200 $\mu m^2$, in order to assure the electrolyte loss is as small as possible.

If only a single bore, which can be produced in the housing wall, for example, by means of laser ablation, is provided, then the bore diameter at its narrowest point can be about 1 $\mu m$ up to 50 $\mu m$. If an aqueous solution is provided as a reference electrolyte, then the bore diameter of the individual bore is preferably 1 $\mu m$ to 10 $\mu m$, in order to assure the electrolyte loss is as small as possible.

If the separating wall has a number of bores, via which the reference electrolyte is in contact with the surrounding medium, then the diameter at the narrowest points can be between 0.01 $\mu m$ and 10 $\mu m$, especially between 0.1 $\mu m$ and 5 $\mu m$, wherein care is taken that the product of the number of the bores and their cross sectional areas does not exceed the value ranges set forth above. Bores with such small cross sections are manufacturable, for example, through the use of nuclear track etching.

In an additional embodiment, the sensing system comprises a metal wire, especially a silver wire coated with a slightly soluble, silver salt.

In an additional embodiment, the housing comprises an electrically non conductive material, for example, glass or a synthetic material. The housing wall, especially, the wall having the aforesaid bore, advantageously comprises glass or a synthetic material. The aforesaid housing wall can comprise a synthetic foil comprising polyester or polycarbonate, for example. The synthetic foil can have a thickness between 5 $\mu m$ and 50 $\mu m$, preferably between 5 $\mu m$ and 20 $\mu m$, for example.

The housing, which surrounds the housing interior of the reference electrode, can be formed as a single part. However, it can also be a combination of at least a first housing part and a housing wall, which has the aforesaid bore and is connected to the first housing part. The housing wall, which has the aforesaid bore, can, in this case, be connected to the first housing part by a connection impermeable to liquids, especially adhesion, welding or clamping. In the following, the housing wall, which has the bore, is also referred to as a separating wall. The connection impermeable to liquids between the first housing part and the separating wall assures that the electrolyte filled housing interior is in contact with the measured medium exclusively through the at least one bore in the separating wall, not, however, via unsealed connecting locations between the housing part and the separating wall.

In an additional embodiment, the housing wall, which has the aforesaid bore, is essentially embodied as a planar surface or as an essentially dome shaped surface or as a cylindrical surface. For example, the housing can be embodied in the same manner as the housing of a pH glass electrode, i.e. with a housing region essentially embodied as a cylindrical shaft, which is provided with a dome shaped thin glass wall on one end, wherein the bore is located in the region of the dome shaped thin glass wall.

In an embodiment, the housing wall, which has the aforesaid bore, comprises a synthetic material, especially a synthetic material film or glass, wherein the bore is produced by laser ablation. This has the advantage that the bore or bores can be first produced in the film or the thin wall, still separate from the housing, by laser ablation or nuclear track etching, and this can then be connected to the remaining housing part(s) by means of a joining technology impermeable to liquids, for example, by adhesion, welding or press molding. This is technologically simpler to manufacture than a bore in a one piece housing part.

The invention includes furthermore a single rod, measuring chain comprising a reference electrode according one of the embodiments described above and a measuring electrode. The measuring electrode can be, for example, an ion selective electrode, a glass electrode or an ion selective polymer membrane electrode. A chemically sensitive semiconductor component, especially an ion selective field effect transistor (ISFET), can also equally serve as a measuring electrode. The reference electrode forms the reference half cell and the measuring electrode the measuring half cell of the single rod, measuring chain.

In an embodiment of the single rod, measuring chain, the housing of the measuring electrode has a tubular form and surrounds a housing interior, which at least partially accommodates a sensing system for sensing a measured electrode potential, which, for example, in the case of an embodiment of the measuring electrode as a membrane electrode, is in contact with the measuring membrane,
and wherein the reference electrode has a housing surrounding the housing of the measuring electrode and is completely closed off from the housing interior of the measuring electrode.

Furthermore, the invention relates to a flow through cell with a reference electrode according to one of the embodiments described above integrated into the flow through cell, wherein the reference electrode is integrated in at least a first housing part of the flow through cell, and wherein the wall, which has the aforesaid at least one bore, is connected to the first housing part by a connection impermeable to liquids and borders on a hollow space during operation of the flow through cell flowed through by the measured medium.

In an embodiment of the flow through cell, the hollow space is bordered by the wall, which has the at least one bore, and by at least one surface of a second housing part, wherein the second housing part includes a liquid supply and a liquid drain, which open into the hollow space.

In an alternative to this embodiment of the flow through cell, the hollow space is bordered by the wall, which has the at least one bore, and by at least one surface of a second housing part, as well as an especially annular spacer between the first and the second housing parts, wherein the second housing part includes a liquid supply and a liquid drain, which open into the hollow space.

BRIEF DESCRIPTION OF THE DRAWINGS

The invention will now be explained in greater detail based on the examples of embodiments illustrated in the drawing. The figures of the drawing show as follows:

FIG. 7 is a schematic, longitudinal section of a second example of an embodiment of a reference electrode;

FIG. 8 is a schematic, longitudinal section of a third example of an embodiment of a reference electrode;

FIG. 10 is a schematic, longitudinal (a) and cross sectional (b) representations of a flow through cell having an integrated reference electrode.

DETAILED DISCUSSION IN CONJUNCTION WITH THE DRAWINGS

Figure 1:
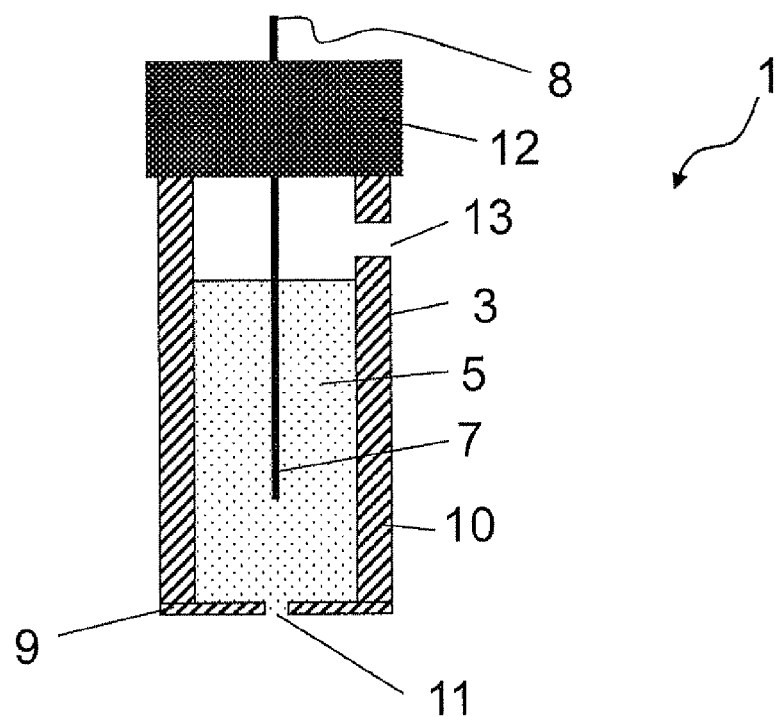
FIG. 1 is a schematic, longitudinal section of a reference electrode containing in a housing a reference electrolyte, which is in contact with a surrounding medium via a traversing bore in a housing wall.

FIG. 1 shows schematically a longitudinal section through a reference electrode 1 having a tubular housing portion 10, which is provided a closure cap 12 on one end and with a separating wall 9 connected at the other end to the tubular housing portion 10 to form a housing 3. The tubular housing portion 10, the closure cap 12 and the separating wall 9 define a housing interior, which is filled, for example, in a region adjoining the separating wall 9, with a reference electrolyte 5 in the form of an aqueous, 3 molar, potassium chloride solution. A silver wire coated with silver chloride serves as a sensor 7 extending into the reference electrolyte 5. Sensor 7 is led through the closure cap 12 and connected to a measuring electronics (not shown) via a connection wire 8. For example, the connection wire 8 can be led to a high impedance input of a measuring amplifier or impedance converter, which outputs the electrode potential as a voltage signal and forwards the amplified or converted voltage signal to a superordinated unit, e.g. a measurement transmitter or bus coupler, for analog/digital conversion, display and processing.

Reference electrolyte 5 is in contact with the environment of the reference electrode 1 via a traversing bore 11 in separating wall 9. In measurement operation, a housing region of the reference electrode 1 surrounding the separating wall 9 is immersed in a measured medium so that the reference electrolyte 5 comes in contact with the measured medium via the bore 11.

Bore 11 preferably has a cylindrical or conical shape and a circularly shaped cross section with a diameter of 1 to 50 μm at its narrowest point. The separating wall 9 has a thickness of 1 to 200 μm, especially of 1 to 50 μm. One known possibility for implementing such bores is drilling a synthetic foil by means of laser ablation. The drilled film can be adhered to the lower, open end of the tubular housing portion 10, in order to form a housing 3, which surrounds a housing interior, which contains a reference electrolyte. Alternatively, for example, in the case of a housing formed in one piece, a traversing bore can also be produced directly in a housing wall by means of laser ablation or electrical discharge machining.

A bore 11 with the dimensions set forth here is distinguished by a short diffusion path of a few multiples of 10 to a maximum of a few multiples of 100 μm. The diffusion path includes, in such a case, the entire length of bore 11 as well as the two adjoining diffusion zones at the exit of bore 11 into the housing interior and at the exit of bore 11 into the housing environment, for example, into the measured medium. A short diffusion path leads to a rapidly steady state concentration profile and therewith also a constant diffusion potential through the diaphragm. After immersion of the reference electrode into the measured medium or after a change of composition of the measured medium, the diffusion potential adjusts faster than in the case of other types of diaphragms, especially in the case of diaphragms which have extended diffusion zones with a length of many mm or even cm.

Figure 2:
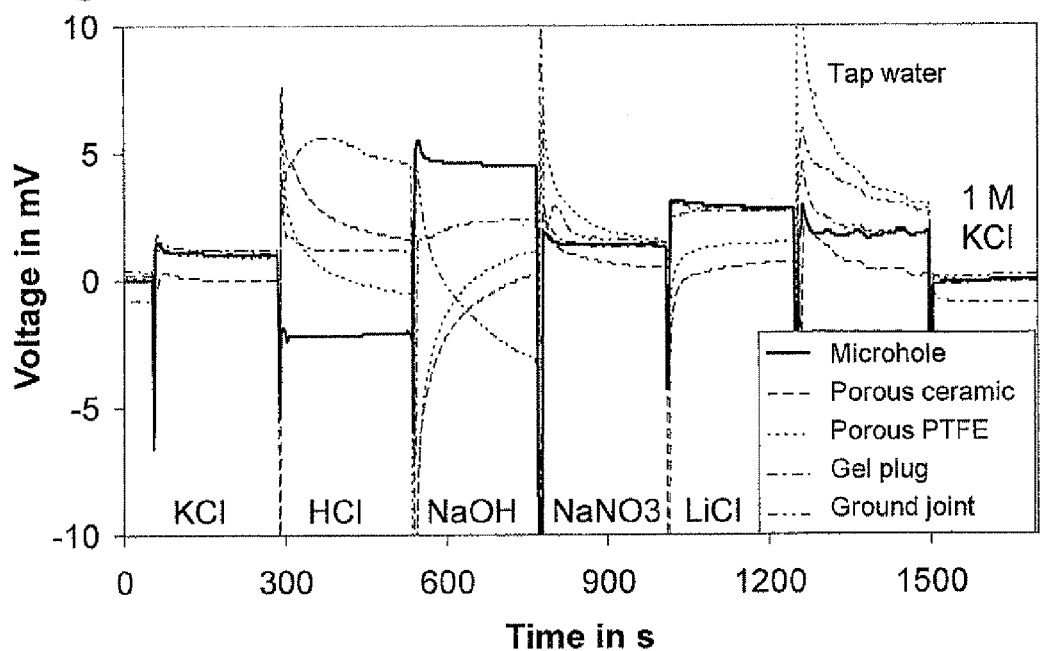
FIG. 2 is a graph of voltage as a function of time registered by a plurality of reference electrodes with different diaphragms immersed in different measured media.

This is illustrated with FIGS. 2 to 5. FIG. 2 shows the curve of electrode potential as a function of time after immersion of a plurality of experimental electrodes with different types of diaphragms into different measured media. The experimental electrodes all possess a housing filled with a 3 molar potassium chloride solution as reference electrolyte (in the case of some of the experimental electrodes the reference electrolyte is thickened or solidified by a gel additive) and containing, extending into the reference electrolyte, a potential sensor in the form of a silver wire coated with silver chloride sensor. In a first experimental electrode, a traversing bore in a housing wall served for electrolytic contact between the reference electrolyte and measured medium, similar to the reference electrode as in FIG. 1 (solid line); in a second experimental electrode, a diaphragm of porous ceramic (dashed line) served for electrolytic contact between the reference electrolyte and measured medium; in a third experimental electrode, a diaphragm of porous PTFE (dotted line) served for electrolytic contact between the reference electrolyte and measured medium: in a fourth experimental electrode, a gel plug (dash dot line) and in a fifth experimental electrode, a ground glass diaphragm (dash dot dot line) served for electrolytic contact between the reference electrolyte and measured medium. The first experimental electrode has a housing wall formed from a 12 μm thick Melinex® film, which is provided, for instance, with a traversing bore with a 3.5 μm inner diameter ("microhole").

The measured media were, respectively, 0.1 molar aqueous solutions of KCl, HCl NaOH, NaNO$_3$, LiCl, as well as tap water and a 1 molar aqueous solution of KCl. Each experimental electrode was immersed in each measured medium one after the other. The electrode potentials of the five experimental electrodes were measured against a shared reference electrode, which continually stood in connection with each of the measured media via an agar gel, salt bridge. Thus, the time response of the agar gel, salt bridge is not significant in this experimental setup. It is evident from FIG. 2 that the potential of the first experimental electrode (solid line) stabilized, without exception, faster after immersion in a measured medium than the other experimental electrodes used for comparison.

Figure 3:
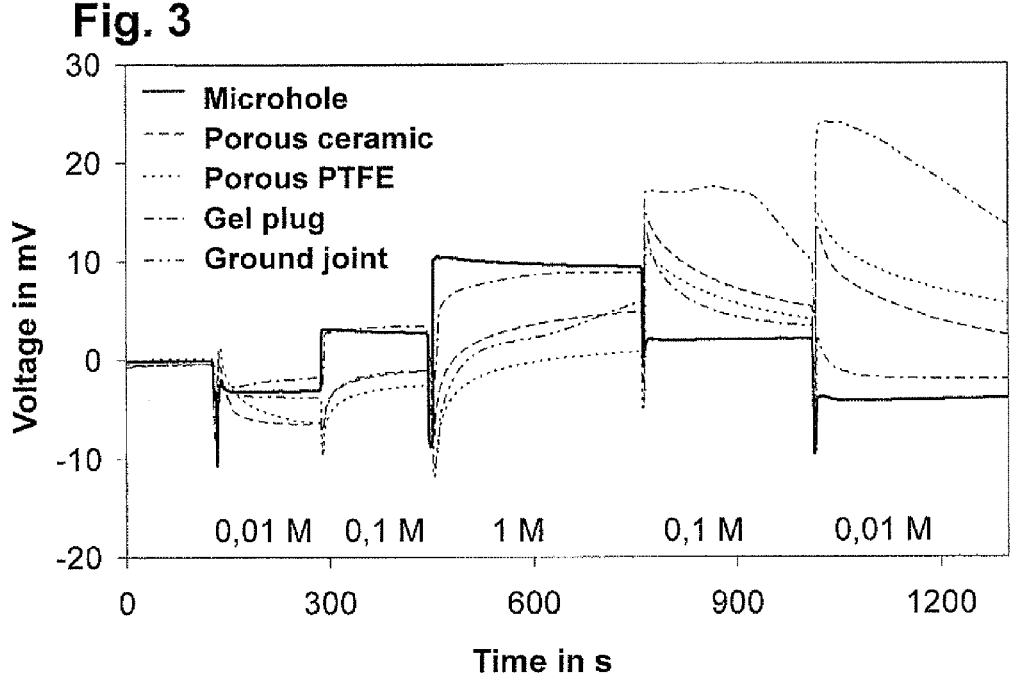
FIG. 3 is a graph of voltage registered by a plurality of reference electrodes with different diaphragms immersed in magnesium chloride solutions of different concentrations.

In a similar experiment with the same set of experimental electrodes, the electrode potential of the different experimental electrodes was measured as a function of time after immersion in aqueous magnesium chloride solutions of different concentrations. The potential curves obtained are shown in FIG. 3. It can also be observed here that the first experimental electrode with the traversing bore as a diaphragm clearly reaches a constant potential faster than the remaining experimental electrodes.

Figure 4:
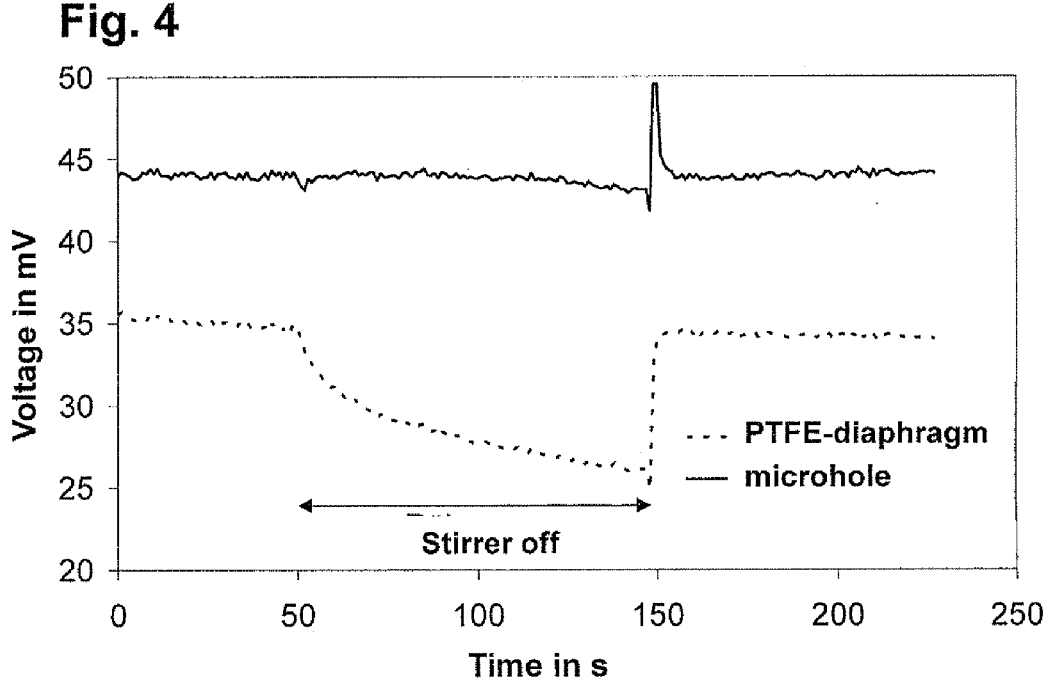
FIG. 4 is a graph of measurement voltage as a function of time in demineralized water for a first pH measuring chain with a reference electrode as in FIG. 1 and a second pH measuring chain with a comparison reference electrode having a porous diaphragm.

FIG. 4 shows measurement voltage curves as a function of time for two pH measuring chains, in each case having a pH selective electrode as measuring electrode and a silver/silver chloride reference electrode in demineralized water. The reference electrode of the first pH measuring chain has a traversing bore (solid line) with a length of, for instance, 12 µm and an inner diameter of, for instance, 3.5 µm ("microhole"), in a housing wall serving as a diaphragm as in the reference electrode shown in FIG. 1. The reference electrode of the second pH measuring chain has, as diaphragm, a conventional, porous PTFE diaphragm (dashed line). The measurement curves shown in FIG. 4 were recorded simultaneously using a shared pH measuring electrode so that only the establishing of the reference electrode potential is important for establishing the measurement voltage of each measuring chain. The measured medium was stirred at the beginning the experiment, then, at 50 seconds, the stirrer was turned off and after passage of 100 seconds turned back on. While the measurement voltage of the measuring chain with the reference electrode with a PTFE diaphragm immediately changed after turning off the stirrer and after about 100 seconds has about an 8 mV drift, practically no change was detectable in the other measuring chain.

Figure 5:
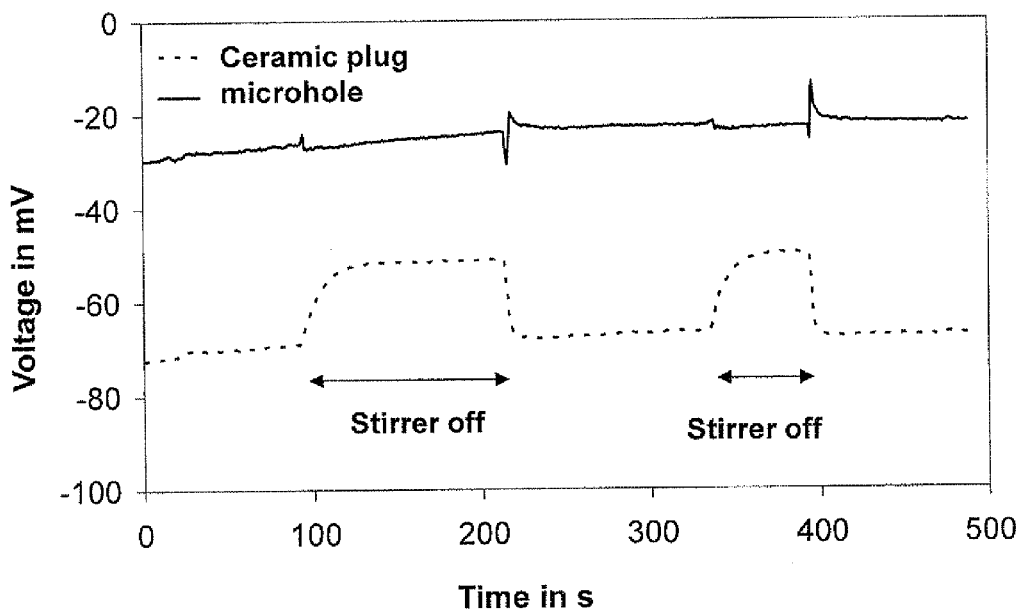
FIG. 5 is a graph of measurement voltage as a function of time in tap water for a first pH measuring chain with a reference electrode as in FIG. 1 and a second pH measuring chain with a comparison reference electrode having a porous diaphragm.

An analogous experiment was performed with almost the same experimental arrangement in tap water, wherein the reference electrode of the second measuring chain was replaced by an otherwise equally constructed reference electrode but having a ceramic plug diaphragm. The measured voltage curves are shown in FIG. 5. Immediately after turning off the stirrer after 100 seconds, or after 340 seconds, a rise of the measurement voltage in the second measuring chain of about 18 mV is to be seen. With the first measuring chain with the reference electrode according the type shown in FIG. 1, a substantially smaller rise of the measurement voltage was detected, which, moreover, also fell back to almost the original value after just a few seconds.

It is clearly to be seen from the experimental data illustrated in FIGS. 2 to 5 that a reference electrode of the type shown in FIG. 1 not only required a shorter time for reaching a constant electrode potential, but also that this electrode potential is also largely independent of the flow velocity of the measured medium and is subject to a clearly smaller drift than the electrode potentials of conventional reference electrodes with a porous ceramic or plastic diaphragm.

Figure 6:
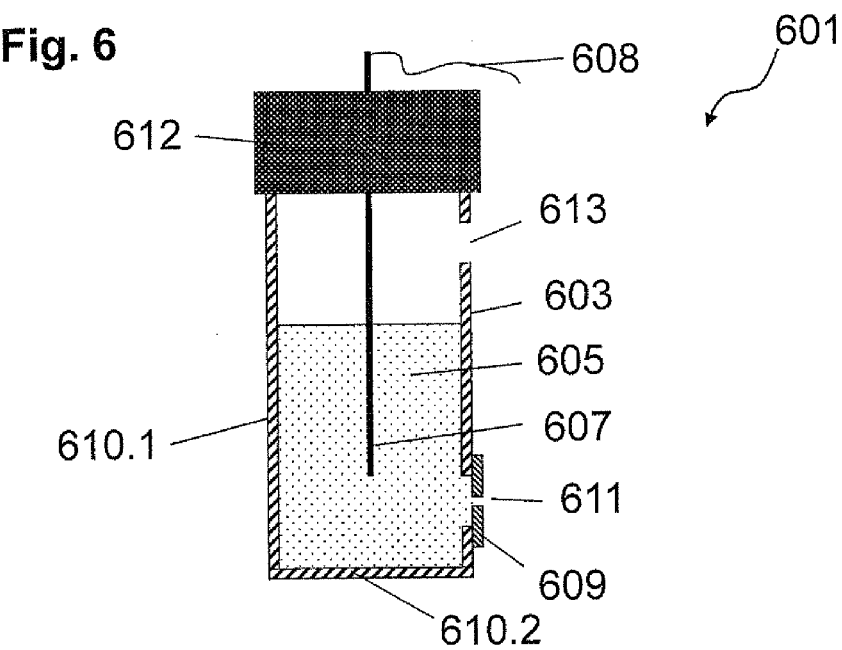
FIG. 6 is a schematic, longitudinal section of a first example of an embodiment of a reference electrode.

FIG. 6 shows schematically a longitudinal section through a further example of an embodiment. Reference electrode 601 includes a first tubular housing portion 610.1 of a synthetic material, e.g. plastic. The outer diameter of the tubular housing portion 610.1 can be, for example, 12 mm with the length of the tubular housing portion 610.1 being 12 cm. On its first end, the tubular housing portion 610.1 is sealed by a closure cap 612 and on its second end, opposite the first end, it is sealed with a disk shaped, second housing portion 610.2. In the region of the second end, the tubular housing portion 610.1 includes a circular opening of 3 mm diameter, which is covered by a separating wall 609 secured to the housing exterior of the tubular housing portion 610.1. This separating wall 609 has a thickness of 12 µm, and can be embodied as a polyester film, for example. The tubular housing portion 610.1, the second housing portion 610.2 and the separating wall 609 form a housing 603 surrounding a housing interior, which contains the reference electrolyte 605. Via a traversing bore 611 (for example, one produced by means of laser ablation) in the separating wall 609, the reference electrolyte 605 is in contact with a medium surrounding the housing 603 in the region of the bore 611. For measurement operation, the housing 603 of the reference electrode 601 is immersed in the measured medium at least in a region around the traversing bore 611. Bore 611 has a conical shape and an inner diameter of 2 µm at the point of its smallest cross section. The region of the smallest cross section of the conical bore 611 is its exit to the measured medium.

A silver wire coated with silver chloride and immersed in the reference electrolyte 605 serves as sensor 607. Sensor 607 is led through the closure cap 612 and connected to measuring electronics (not shown) by a connection wire 608. The wall of the first, tubular housing portion 610.1 includes, in the region of the connection end, a replenishment opening 613, through which reference electrolyte in the housing interior can be replenished. Usually, the replenishment opening 613 is closable by means of a stopper.

FIG. 7 shows schematically in longitudinal section an additional embodiment in the form of a reference electrode 701. Reference electrode 701 includes a tubular housing portion 710 with a length of 12 cm and outer diameter of 12 mm, with a closure cap 712 on one end and on the other end a separating wall 709 embodied as a polyester film connected to the housing portion 710 by welding to form a housing 703 impermeable to liquids. The polyester film has a thickness of 12 µm, and is provided at its center with a conical, traversing bore 711, which has an inner diameter of about 5 µm in the region of its narrowest cross section. This region preferably forms the exit of the bore 711 to the housing environment.

The housing interior is completely filled with a form-stable gel, reference electrolyte 705. A suitable gel reference electrolyte 705 can be produced in the housing of the reference electrode, for example, by cross linking polyacrylamide in a 3 molar aqueous solution of potassium chloride. If the region comprising the separating wall 709 of the reference electrode 701 is immersed in a measured medium, the gel reference electrolyte 705 is in contact with the measured medium via the bore 711. The potential sensor 707 is formed by a silver wire coated with silver chloride. As in the examples in FIGS. 1 and 6, sensor 707 is led through the closure cap 712 and is connected to measuring electronics by a connection wire 708.

Since the housing interior of the reference electrode 701 is completely filled with gel reference electrolyte 705, the reference electrode 701 can also be applied at increased pressures without being sensitive to pressure fluctuations. If the housing 703 and the electrolyte 705 strongly expand differently as a result of temperature fluctuations, there is a small deformation of the polyester film separating wall 709, whereby discharge of the reference electrolyte 705 or absorption of the measured medium into the housing interior is prevented.

FIG. 8 shows in longitudinal section a further example of an embodiment in the form of a reference electrode 801. Reference electrode 801 includes a glass tubular housing portion 810 with an outer diameter of about 12 mm and a length of about 12 cm, sealed on one end with a closure cap 812, with, connected on its opposite end, a dome shaped housing wall 809, to form a housing 803 surrounding a housing interior. The dome shaped housing wall 809 is likewise made of glass. A viscous reference electrolyte 805, for example in the form of a 3 molar aqueous solution of potassium chloride thickened by addition of 3% polyacrylamide, is provided in the housing interior. The reference electrolyte 805 is in contact with the environment of the housing 803 via a traversing bore 811 in the dome shaped housing wall 809. The dome shaped housing wall has a wall thickness of about 100 µm in the region of the bore 811, so that the length of the bore 811 is likewise no more than 100 µm. The cross section of the bore 811 possesses a diameter of 10 µm. Such a bore can be produced by laser ablation, for example.

As described above, a potential sensor 807 comprising a silver wire coated with silver chloride is immersed in the reference electrolyte 809 and led through the closure cap 812 and connected to a measuring electronics via a connection wire 808. The housing 803 includes a round replenishment opening 813 in the region of its connection end for replenishment of reference electrolyte into the housing interior.

Figure 9:
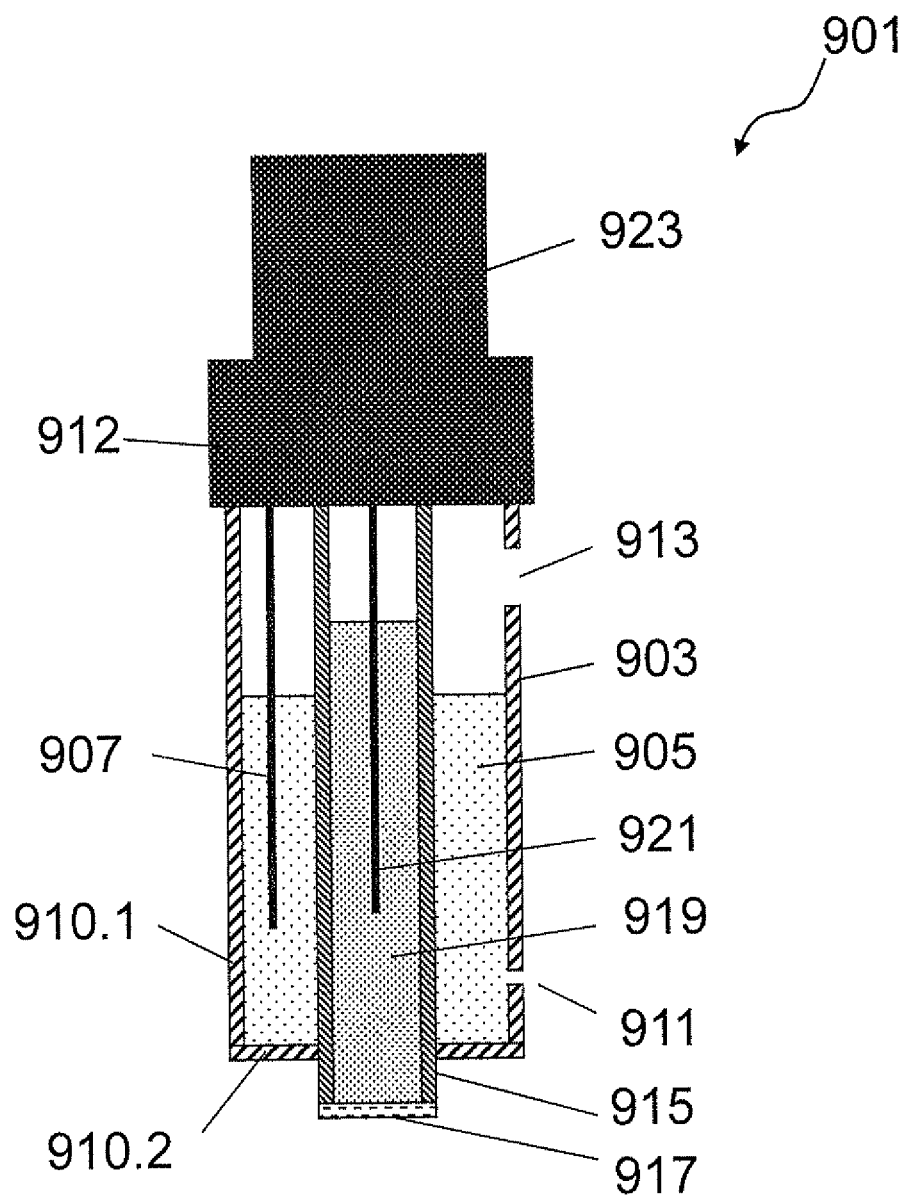
FIG. 9 is a schematic, longitudinal section of a single rod, measuring chain with an ion selective membrane electrode as a measuring half cell and a reference electrode, whose reference electrolyte is in contact with the measured medium via a traversing bore in the housing wall.

FIG. 9 shows a single rod, measuring chain 901 including a membrane electrode as a measuring half cell and a reference electrode as reference half cell. The measuring half cell of the single rod, measuring chain 901 includes a first tubular housing portion 915 with an inner diameter of 4 mm and a length of 12 cm made from an electrically non conductive material, glass in the example described here. The first tubular housing portion 915 is closed by a sensor plug head 923 at its first end region and by an ion selective membrane 917 at its second end region, and so defines a first housing interior, the measuring half cell interior. The sensor system of the measuring half cell is formed by a liquid inner electrolyte 919 in which a potential sensor 921, a metal wire, for example, is immersed. Sensor 921 is connected to measuring electronics accommodated in the sensor plug head 923. The measuring half cell can be, for example, a conventional pH selective, glass membrane electrode.

Tubular housing portion 915 is surrounded by an outer tube 910.1 of glass or plastic with an outer diameter of 12 mm. Outer tube 910.1 is arranged concentrically with the tubular housing portion 915 and is closed by the sensor plug head 923 on its one end; the end opposite to the sensor plug head 923 is bounded by an annular end housing wall 910.2, which is connected with the outside of the tubular housing portion 910.1. The outer tube 910.1, the tubular housing portion 915, the sensor plug head 923 and the annular end housing wall 910.2 thus surround a second housing interior, the reference half cell interior. The reference half cell interior is at least partially filled with a reference electrolyte 905, a 3 molar aqueous potassium chloride solution, for example, in which is immersed an outer potential sensor 907, for example, a silver wire coated with silver chloride. The outer sensor 907 is conductively connected to the electronic circuit accommodated in the sensor plug head 923. The electronic circuit conditions the potentials delivered by sensors 613 and 633 and forwards the conditioned signals.

Tube 910.1 includes, in its plug head region, a replenishment opening 913, through which the reference electrolyte 905 in the reference half cell interior can be replenished. Advantageously, the replenishment opening 913 is closable by a valve or stopper (not shown). In the end region opposite the sensor plug head 923, the tube 910.1 includes a traversing bore 911 with an inner diameter of 5 µm at the point of its smallest cross section. At least in this end region, the tube 910.1 possesses a wall thickness of only 200 µm, so that the traversing bore 911 has a length of only 200 µm. In an alternative embodiment, the tube can also possess a larger wall thickness. In this case, the tube can have an opening some millimeters in diameter, which is covered by a thin film less than 200 µm thick, wherein the film has a traversing bore with an inner diameter of 5 µm, via which the reference electrolyte is in contact with the environment of the single rod, measuring chain 901.

For performing concentration measurements or pH measurements, an immersion region on the end opposite the sensor plug head 923 of the single rod, measuring chain 901 is brought in contact with a measured medium. This immersion region includes both the ion selective membrane 917 as well as the traversing bore 911. A temperature sensor (not shown) can optionally be provided in the single rod, measuring chain 901.

The sensor plug head 923 forms the primary side of a pluggable connector coupling, via which the single rod, measuring chain is connected to a superordinated unit, a measurement transmitter, for example. The conditioned signals can be transmitted to the superordinated unit and there further processed and/or output. The pluggable connector coupling can be embodied as a plug contact with galvanic coupling, or, for minimizing electrical disturbing influences, a plugged connection with inductive signal and energy transmission.

A flow through cell for online measurements with a reference electrode is schematically shown in FIG. 10 in longitudinal section (FIG. 10 *a*)) and in cross section based on the cutting plane A (FIG. 10 *b*)). The flow through cell can be used, for example, in an analytical system or an analyzer, for example, according to the embodiment described in European patent application EP 1 509 774 A1. It can be connected to one or a plurality of additional similarly built flow through cells with ion or pH value selective measuring electrodes in such a manner that a measured medium flows through all connected flow through cells in measurement operation and therefore a measuring chain for measuring pH value and/or ion concentration is formed with respect to the reference electrode.

The flow through cell includes a first pot shaped housing portion 1025, which together with a separating wall 1009, formed from a 12 µm thick polyester film, for example, and fixedly connected to the pot shaped housing portion 1025, bounds a housing interior. The housing interior is completely filled with a reference electrolyte 1005 in the form of a 3 molar aqueous potassium chloride solution gelled through the addition of, for example, cross linked polyacrylamide. Via a conical bore 1011 with an inner diameter of 5 µm at its narrowest point in the separating wall 1009, the reference electrolyte 1005 is in contact with a measuring chamber 1026, through which a measured medium flows in measurement operation, as further described below. The narrowest point of the conical bore 1011 preferably forms the exit to the measuring chamber 1026. The sensing of the electrode potential arising in measurement operation occurs by means of a sensor 1007 in the form a silver wire coated with silver chloride and protruding into the reference electrolyte 1005. Sensor 1007 is led through the first housing portion 1025, and connected to measuring electronics (not shown).

Since the entire housing interior is filled with the gel reference electrolyte 1005, the stability of the reference electrode is also assured in the case of high or low pressure in the measuring chamber 1026. In the case of temperature changes, the reference electrolyte and the housing can expand or contract without the measured medium being pressed in from the measuring chamber 1026 into the housing interior or the reference electrolyte 1005 being pressed out from the housing interior, due to the flexibility and elasticity of the separating wall 1009 embodied as a film.

The supply line 1033 serves for filling the housing interior with the reference electrolyte 1005 and can be sealed against the environment by means of a valve 1035. By way of example, polytetrafluoroethylene (Teflon PTFE) is a possibility as a material for the first housing portion 1025.

The measuring chamber 1026 is bordered by the separating wall 1009, a second housing portion 1028 of e.g. polymethylmethacrylate (Plexiglass PMMA) and an annular spacer 1027 of e.g. polytetrafluoroethylene. The second housing portion 1028 is provided with a supply line 1029 and a drain 1030 for a measured medium, which flows through the measuring chamber 1026 in measurement operation of the flow through cell.

As indicated above, the flow through cell can be connected to a second essentially equally constructed flow through cell (not shown) in such a manner that the measured medium flows through both measuring chambers of the flow through cells in measurement operation. The second flow through cell can possess, for example, a pH or ion selective membrane instead of the separating wall 1009. In the case of such a construction with two flow through cells, the first flow through cell forms a reference half cell and the second flow through cell forms a measuring half cell. With this construction, for instance, a pH value or an ion concentration of the measured medium flowing through can be determined. Of course, a number of equally constructed measuring half cells can also be connected to the reference half cell in order, in this way, to simultaneously determine the concentrations of various ions, for example, ammonium and nitrate ions, and/or the pH value, in the flowing measured medium.

The invention claimed is:

1. A reference electrode, especially for a potentiometric measuring cell, comprising:
  a sensing system for sensing a potential of the reference electrode; and
  a housing, which surrounds a housing interior, which contains a reference electrolyte and at least a part of said sensing system; wherein:
  the reference electrolyte is in contact with a medium surrounding said housing, especially a measured medium, via at least one traversing bore through a housing wall of said housing;
  said bore has an inner diameter of no more than 50 µm at its narrowest point and a length of no more than 200 µm; and
  wherein the reference electrolyte is a gel reference electrolyte.

2. The reference electrode as claimed in claim 1, wherein:
  said bore has a cylindrical or conical shape with a circularly shaped or almost circularly shaped cross section.

3. The reference electrode as claimed in claim 1, wherein:
  the reference electrolyte is in contact with the medium surrounding said housing via said traversing bore or a number of traversing bores through the housing wall of said housing; and
  the sum of the cross sectional areas of all traversing bores at the narrowest points of each is between 0.5 µm$^2$ and 2000 µm$^2$.

4. The reference electrode as claimed in claim 3, wherein:
  the sum of the cross sectional areas of all traversing bores at the narrowest points of each is between 0.5 µm$^2$ and 20 µm$^2$.

5. The reference electrode as claimed in claim 1, wherein:
  the reference electrolyte is in contact with the medium via said bore; and
  the diameter at its narrowest point is between 1 µm and 50 µm.

6. The reference electrode as claimed in claim 1, wherein:
  the reference electrolyte is in contact with the medium via a number of bores; and
  the diameter of each individual bore at its narrowest point is between 0.01 µm and 10 µm.

7. The reference electrode as claimed in claim 1, wherein:
  said sensor system comprises a metal wire, especially a silver wire coated with a slightly soluble silver salt.

8. The reference electrode as claimed in claim 1, wherein:
  said housing wall, which has said bore, is connected to an additional housing portion with a joint impermeable to liquids in order to form said housing.

9. The reference electrode as claimed in claim 8, wherein:
  the joint is formed by adhesion, welding or clamping.

10. The reference electrode as claimed in claim 1, wherein:
  said housing wall, which has said bore, is essentially embodied as a planar surface or an essentially dome shaped surface or a cylindrical surface.

11. The reference electrode as claimed in claim 1, wherein:
  said housing wall, which has said bore, comprises a synthetic material or glass; and
  said bore is produced by means of laser ablation.

12. A single rod, measuring chain comprising a reference electrode and a measuring electrode,
  wherein the reference electrode comprises:
  a sensing system for sensing a potential of the reference electrode; and
  a housing, which surrounds a housing interior, which contains a reference electrolyte and at least a part of said sensing system; and wherein:
  the reference electrolyte is in contact with a medium surrounding said housing, especially a measured medium, via at least one traversing bore through a housing wall of said housing; and
  said bore has an inner diameter of no more than 50 µm at its narrowest point and a length of no more than 200 µm.

13. The single rod, measuring chain as claimed in claim 12, wherein:
  the measuring electrode is embodied as a membrane electrode, especially a pH glass electrode or an ion selective polymer membrane electrode, or as a chemically sensitive semiconductor component.

14. The single rod measuring chain as claimed in claim 13, wherein:
  said chemically sensitive semiconductor component is an ion selective field effect transistor (ISFET).

15. The single rod, measuring chain as claimed in claim 12, wherein:
  the housing of the measuring electrode has a tubular form and surrounds a housing interior, in which a sensing system for sensing a measuring electrode potential is at least partially accommodated; and
  the reference electrode has a housing surrounding the housing of the measuring electrode and completely closed to the housing interior of the measuring electrode.

16. The single rod measuring chain as claimed in claim 12, wherein:
  the reference electrolyte is a gel reference electrolyte.

17. A flow through cell with a reference electrode integrated into the flow through cell, wherein:
  said reference electrode comprises:
  a sensing system for sensing a potential of the reference electrode; and
  a housing, which surrounds a housing interior, which contains a reference electrolyte and at least a part of said sensing system; and wherein:
  the reference electrolyte is in contact with a medium surrounding said housing, especially a measured medium, via at least one traversing bore through a housing wall of said housing; and
  said bore has an inner diameter of no more than 50 µm at its narrowest point and a length of no more than 200 µm; and
  the reference electrode is integrated into at least a first housing portion of the flow through cell; and the wall, which has the at least one bore, is connected with the first housing portion by means of a liquid tight connection and borders a hollow space through which the measured medium flows in measurement operation.

18. The flow through cell as claimed in claim 17, wherein:

the hollow space is bordered by the wall, which has at least one bore, and by at least one area of a second housing portion; and the second housing portion has a liquid supply and a liquid drain that open into the hollow space.

19. The flow through cell as claimed in claim 17, wherein:

the hollow space is bordered by the wall, which has the at least one bore, and by at least one area of a second housing portion, as well as a spacer, between the first and the second housing portion; and the second housing portion has a liquid supply and a liquid drain that open into in the hollow space.

20. The flow through cell as claimed in claim 19, wherein: said spacer is an annular spacer.

21. The single rod measuring chain as claimed in claim 17, wherein:

the reference electrolyte is a gel reference electrolyte.

\* \* \* \* \*